United States Patent
Bambini et al.

(10) Patent No.: US 8,683,693 B2
(45) Date of Patent: Apr. 1, 2014

(54) DENTAL IMPLANT APPARATUS, SCREW FOR DENTAL IMPLANT APPARATUS AND METHOD OF MAKING A SCREW

(71) Applicants: Fabrizio Bambini, Senigallia (IT); Andrea Santarelli, Jesi (IT); Angelo Putignano, Ancona (IT); Maurizio Procaccini, Rome (IT); Monica Emanuelli, Ancona (IT)

(72) Inventors: Fabrizio Bambini, Senigallia (IT); Andrea Santarelli, Jesi (IT); Angelo Putignano, Ancona (IT); Maurizio Procaccini, Rome (IT); Monica Emanuelli, Ancona (IT)

(73) Assignee: Supercharged Production S.R.L., Senigallia (IT)

( * ) Notice: Subject to any disclaimer, the term of this patent is extended or adjusted under 35 U.S.C. 154(b) by 0 days.

(21) Appl. No.: 13/837,752

(22) Filed: Mar. 15, 2013

(65) Prior Publication Data
US 2013/0203017 A1     Aug. 8, 2013

Related U.S. Application Data

(63) Continuation-in-part of application No. 13/138,866, filed as application No. PCT/EP2010/054946 on Apr. 15, 2010, now abandoned.

(30) Foreign Application Priority Data

Apr. 17, 2009   (IT) .............................. MC2009A0083

(51) Int. Cl.
*A61C 8/00*     (2006.01)
*B23P 17/00*    (2006.01)

(52) U.S. Cl.
USPC .......... 29/896.1; 29/527.3; 433/174; 433/189

(58) Field of Classification Search
USPC ....................... 29/527.1, 527.2, 527.3, 896.1; 72/342.5; 264/19; 433/173, 174, 201.1, 433/189
See application file for complete search history.

(56) References Cited

U.S. PATENT DOCUMENTS

| | | | | |
|---|---|---|---|---|
| 4,459,262 A | * | 7/1984 | Komar Kalmar | 420/436 |
| 6,032,677 A | * | 3/2000 | Blechman et al. | 128/899 |
| 6,932,607 B2 | | 8/2005 | Honkura et al. | 433/189 |
| 2002/0142266 A1 | | 10/2002 | Rogers et al. | 433/173 |
| 2009/0029316 A1 | | 1/2009 | Dunn | |
| 2009/0075236 A1 | | 3/2009 | Towse et al. | 433/174 |
| 2013/0157223 A1 | * | 6/2013 | Benhamou | 433/174 |

FOREIGN PATENT DOCUMENTS

| | | |
|---|---|---|
| DE | 42 33 605 C1 | 6/1994 |
| DE | 10 2006 021 476 B3 | 10/2007 |
| EP | 1 323 394 B1 | 7/2003 |

* cited by examiner

*Primary Examiner* — Alexander P Taousakis
(74) *Attorney, Agent, or Firm* — Lowe Hauptman & Ham, LLP

(57) ABSTRACT

A dental implant apparatus including an implant having an external threaded wall adapted to be implanted in a patient's bone, said implant being provided with a cylindrical axial cavity having an internal thread accessible from a first end. The dental implant apparatus further includes a screw comprising a threaded stem adapted to be helicoidally coupled with the internal thread of said cavity of the implant, wherein said screw is a single piece made entirely of a NdFeB (Neodymium-Iron-Boron) compound comprising silicon.

9 Claims, 3 Drawing Sheets

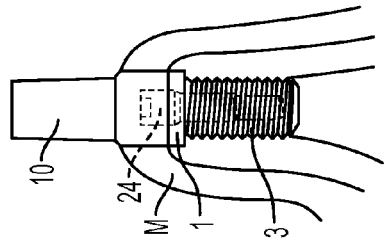
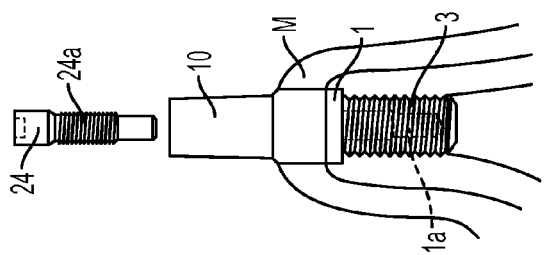
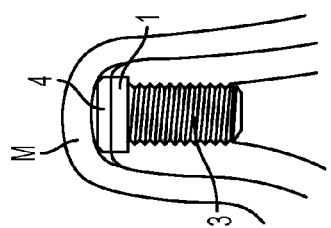
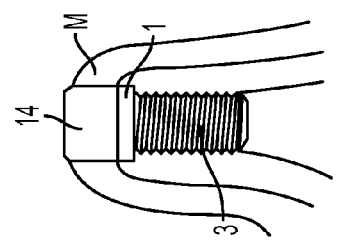
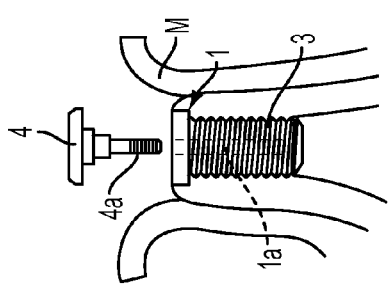
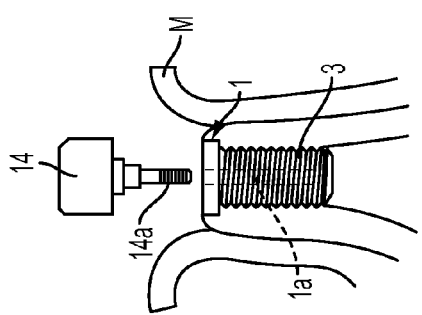

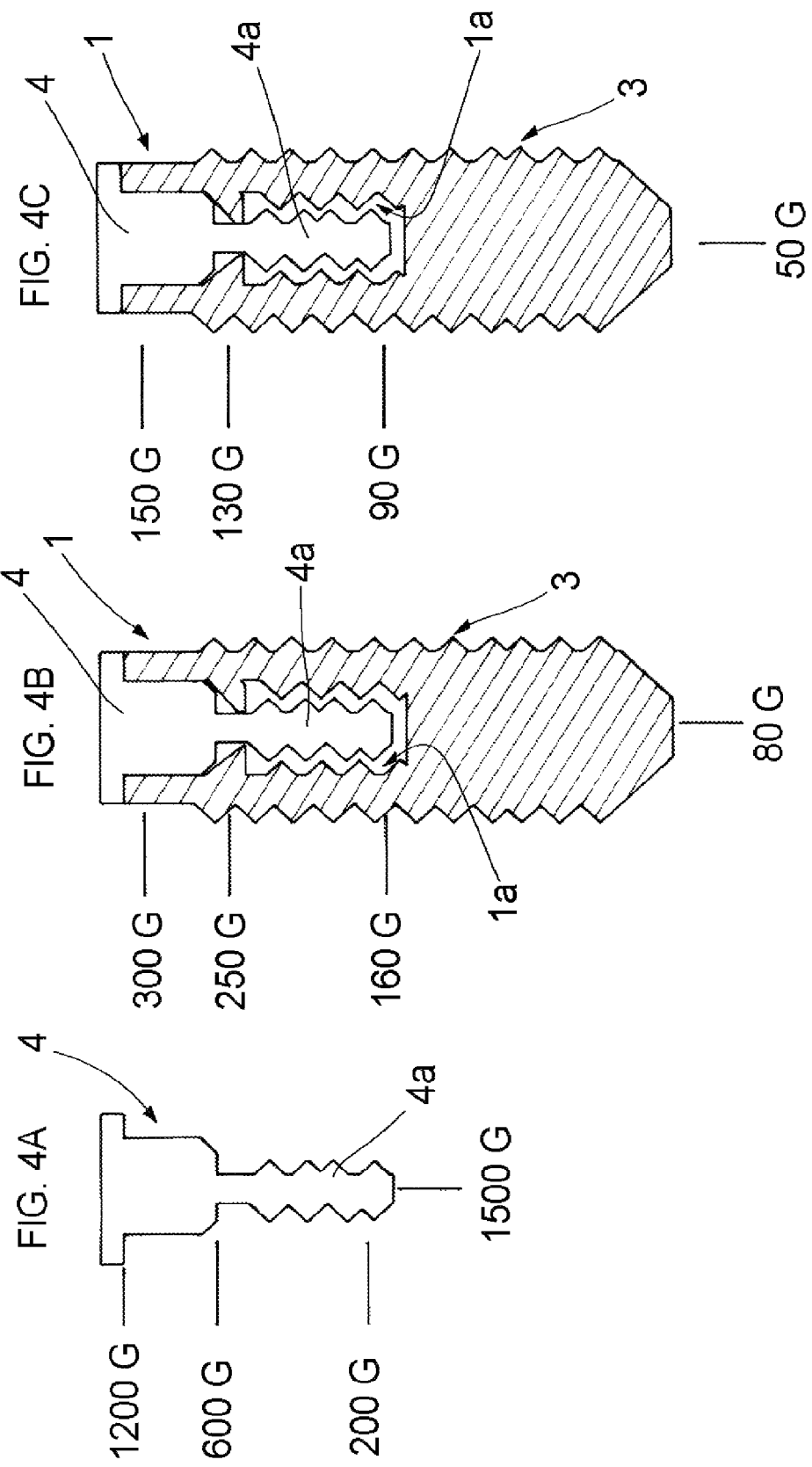

DENTAL IMPLANT APPARATUS, SCREW FOR DENTAL IMPLANT APPARATUS AND METHOD OF MAKING A SCREW

RELATED APPLICATIONS

The current application is a continuation-in-part of U.S. application Ser. No. 13/138,866, filed on Oct. 28, 2011, which is incorporated herein by reference in its entirety.

The present patent application for industrial invention relates to an apparatus for dental implants.

When a patient has lost one or more teeth, for natural or accidental causes or because of dentist's extraction, rehabilitation is often carried out by means of prosthesis.

To that purpose, the dentist implants a basically cylindrical metal pin (technically defined as "implant") in the patient's bone, which acts as a root for the artificial tooth to be installed. The implant is basically an empty cylindrical pin accessible from an upper opening, which is provided with threaded internal walls.

Once such an implant is integrated into the bone, the lowered threaded section of a metal stem, technically defined as "stump", is screwed onto the implant.

In case of threadless stumps, a through screw (technically defined as a "retention screw") is screwed onto each implant in order to fix the stump.

In any case, such a stump is adapted to support the mobile or fixed prosthesis.

The application of such a stump to the corresponding implant cannot be made until the implant is efficaciously integrated and consolidated into the patient's bone. Such a consolidation presumes the healing and reconstitution of bone tissue all around the implant.

In view of the above, the implant must be maintained closed or protected for a time necessary for consolidation by means of a "covering screw" that will be removed when consolidation has been completed, leaving space for the final stump.

For the entire time necessary for consolidation, said covering screw is positioned under the gingival mucosa, suitably stitched on the covering screw by the dentist who has implanted the implant. This means that the removal of said covering screw can take place only following to a new incision of said gingival mucosa that, in the meantime, had cicatrized above the same screw.

A different operating method is sometimes used alternatively to this technology, according to which the closing function of the implant is entrusted to a "healing screw." Although the healing screw is designed to be removed to leave space for the final stump, the healing screw is characterized by a significant difference with respect to an ordinary covering screw.

The peculiarity of such a healing screw consists in that the healing screw is provided with a higher head (compared to an ordinary covering screw) that allows for placing the gingival mucosa at higher height, without the need for stitching said mucosa over the healing screw.

Such a device allows for creating a useful space in the mucosa for the subsequent positioning of the stump.

A special clinical protocol, defined as "immediate load", represents another alternative with respect to the aforementioned traditional methods.

According to the "immediate load" protocol, after inserting the implant in the bone, the dentist can eliminate the covering use and position the stump directly without waiting for complete bone healing.

According to the immediate load protocol the stump supports a non-final prosthesis, defined as "temporary", which will be replaced by the "final" prosthesis.

During the first healing phases of the bone tissue, regardless of the type of screw or technique used, an undesired further reabsorption of the bone, technically defined as "peri-implantar reabsorption collar" can be created around the collar and the first implant spires, which can decrease and/or delay the efficacious consolidation of the implant in the patient's bone.

Experience has shown that the natural time of said osseous reconstitution is rather long, in the order of several months.

So far, it is always necessary to let a variable period of time from eight to twenty-four weeks elapse from the insertion of the implant in the bone to the installation of the final prosthesis.

U.S. Pat. No. 6,032,677 describes an implant with a threaded cavity. A small magnetic insert made of a permanent magnet (NdFeB) is glued to a traditional screw in order to be inserted in the cavity. A variable magnetic field generator is applied in external position on the implant in order to make the magnetic insert vibrate with micromovements to increase the stability of the implant, thus favoring healing and bone growth.

The magnetic insert can be used without external generator to generate a static field only with the purpose of reducing pain. In fact, the magnetic insert is small and unable to generate an adequate magnetic field to reduce healing time.

Moreover, the medical glue used to fix the magnetic insert to the screw is less "powerful" than ordinary glue and the surfaces to be coupled are small; therefore, gluing the magnet to the end of the screw is difficult. By removing the screw made of two glued pieces, the magnet at the end can be detached because of friction along the walls of the internal cavity of the implant, remaining blocked inside and making the implant clinically useless.

EP 1 323 394 describes a keeper for a dental implant. The keeper can be made of any one of the various magnetic dental materials that are not subject to corrosion, which are commonly known for the realization of keepers in dental magnetic attachments. These materials are for instance iron-chrome-molybdenum alloys, soft magnetic stainless steel. These alloys are commonly used to make keepers for magnetic attachments: for instance, SUS 444, SUS MX27, and SUS 417J1 alloys that represent steel alloys known as soft-magnetic alloys. Said materials, such as stainless steel, are known as "soft-magnetic materials" in order to differentiate them from "hard-magnetic materials", such as NdFeB that have different physical and, most of all, magnetic characteristics.

In fact, soft-magnetic materials, such as ferromagnetic alloys, are magnetized by an external field, but once the external field is removed, soft-magnetic materials tend to lose magnetization rapidly. Hard-magnetic materials, instead, do not lose magnetization and create a magnetic field themselves (permanent magnets).

The characteristics that describe soft-magnetic steel alloys are the "saturation magnetic flux density" ($B_s$) and magnetic permeability. The characteristics that describe the quality of a permanent magnet are the "remanent magnetic flux density" ($B_r$), which is preferably higher than 1 Tesla for NdFeB, the coercitive force ($H_c$), which is preferably higher than 800 KA/m for NdFeB and the maximum energy product ($BH_{max}$), which is preferably higher than 200 KJ/m$^3$ for NdFeB. Definitively, the keeper material and the NdFeB belong to two different categories of magnetic materials.

The keeper of EP 1 323 394 is made of steel, and not of NdFeB, because the keeper of EP 1 323 394 must realize permanent attachment with the implant and the prosthesis and must have therefore mechanical characteristics with good performance over time. In fact, the acute-angle end of the ring part of the keeper must be subject to elastic deformation when screwing the keeper to match with the implant and prevent losing the keeper; such elastic deformation is possible with a material such as steel alloy, whereas it would not be possible with NdFeB, which would be probably subject to breakage at the acute-angle end.

The magnetic unit of EP 1 323 394 has a magnet nucleus composed of rare earths, such as NdFeB magnets. But the magnetic unit is not shaped as a screw and is not screwed inside the implant.

A specific purpose of some embodiments of the present invention is to considerably reduce the time necessary to complete the installation of a dental implant and/or prevent or repair the "perimplantar reabsorption collar".

Considering that the most critical phase, both in terms of time and result, is the reconstitution of the perimplantar bone tissue, the apparatus of some embodiments of the invention is characterized by a capability to favor reconstitution in considerably shorter time and/or with better quality.

Some embodiments of the present invention are based on the idea of using a magnetic field to stimulate and/or differentiate the bone cells comprised in said perimplantar tissue, being aware that such a stimulation and/or differentiation is actually capable of ensuring faster and better healing of said tissue.

Said magnetic field can be generated in the implant inserted in the bone and can remain active for the time necessary to guarantee tissue reconstitution.

Practically speaking, such a magnetic field is generated by permanently inserting in the cavity of the implant a temporary screw entirely made of a permanent magnet of NdFeB (Neodymium-Iron-Boron) or an NdFeB compound, designed to be removed only after the perfect consolidation of the implant in the surrounding bone tissue.

The magnetic insert designed to be received in the implant inserted in the bone is entirely composed of the relevant healing screw or retention screw or covering screw, suitably made of NdFeB or the NdFeB compound.

To obtain a magnetic screw made of NdFeB or the NdFeB compound in one piece, the applicant has encountered some difficulties. As a matter of fact, there is some technical impairment in the realization of a one-piece screw made of NdFeB or the NdFeB compound.

Gluing one of the magnetic inserts available on the market to the end of the screw is not possible. Magnetic inserts of suitable dimensions must be milled to obtain a permanent magnet that is adjusted to the internal cavity of the implant and then threaded at the end of the magnetic insert must be obtained. The thread can be less resistant than an ordinary non-magnetic screw and therefore less reliable over time. However, considering the temporary use of the magnetic screw (about 1-2 months), the thread obtained in the magnet is sufficient for the necessary stability.

The realization of a NdFeB or NdFeB compound screw is more difficult than a screw made of steel alloy, since NdFeB or NdFeB compound is more difficult to be machined (for example, magnets can only be machined with diamond point mills and under constant water cooling because high temperatures cause magnetization loss). The thread of the NdFeB or NdFeB compound screw can be less resistant than the thread of the steel screw and is less reliable over time. However, considering the temporary use of the magnetic screw (about 1-2 months) the thread obtained in the magnet is sufficient for stability and retention for the necessary time.

Moreover, since the NdFeB or NdFeB compound screw contains neodymium that is easily subjected to oxidation, such screw must be completely or partially coated to increase anti-corrosion properties (in the part in contact with oral mucosa, the part opposite to the threaded part that is screwed inside the implant). A coating is made with a thin layer of nickel, copper, zinc, tin, silver, gold, titanium, resins or compounds of said materials, etc. Said coating must be sufficiently thin, for example lower than 50 micron, not to impair the magnetic qualities of the screw. The coating procedure is not necessary with steel alloys.

The screw entirely made of NdFeB or NdFeB compound permanent magnet according to some embodiments of the invention has various advantages with respect to an insert made of permanent magnet fixed to an ordinary screw.

As a matter of fact, said screw entirely made of permanent magnet is made in such a way to adjust to the internal cavity of the implant, so that the space available inside the implant is completely occupied by magnetic material. This allows for generating a magnetic field around the implant with higher intensity than the one generated by a smaller magnet as when using separate magnet and screw pieces. The intensity of the magnetic field generated by the one-piece magnetic screw is suitable to produce bone healing as desired.

No glue is used, which, although the glue is biocompatible, can be irritating and uncomfortable to use for the operator. The use of the one-piece magnetic screw makes the removal and insertion of the same screw easier.

Moreover, being the magnetic screw a one-piece screw, also the head of the magnetic screw attracts the end of the screwdriver that is used to insert the screw in the internal cavity of the implant, creating a bond that minimizes the risk that the screw may fall in the oral cavity and be swallowed by the patient during the insertion.

The screw entirely made of NdFeB or NdFeB compound has higher magnetic characteristics than a screw made of soft magnetic material. Said higher magnetic characteristics are necessary to generate a magnetic field around the implant with high intensity with respect to the one generated by a screw made of ferromagnetic steel. The intensity of the magnetic field generated by the NdFeB screw is suitable to produce bone healing as desired. Being a permanent magnet, the NdFeB or NdFeB compound screw maintains the magnetic field for the entire time period necessary for bone healing, whereas a screw made of ferromagnetic steel loses magnetization rapidly.

The screw completely made of NdFeB or NdFeB compound is temporary: the screw must be used for 1-2 months to favor bone growth and healing, and is then removed. After such a period, inserting a final screw is possible. The final screw is made of a material other than magnetic steel alloys with better mechanic characteristics in view of the long life (i.e. titanium, which is more compatible than steel or a gold retention screw that can be tightened with lower force thus preserving and increasing the life of internal attachment system of the implants).

For purposes of clarity, the description of the invention continues with reference to the enclosed drawing, which is intended for purposes of illustration only and not in a limiting sense, wherein:

FIGS. 1A and 1B are diagrammatic views that show, in two subsequent operating phases, the installation of at least one embodiment of the invention (using a magnetic covering screw);

FIGS. 2A and 2B are diagrammatic views that show, in two subsequent operating phases, the installation of at least one embodiment of the invention (using a magnetic healing screw);

FIGS. 3A and 3B are diagrammatic views that show, in two subsequent operating phases, the installation of at least one embodiment of the invention (using a magnetic retention screw);

FIG. 4A is a diagrammatic view that shows the magnetic field expressed in Gauss in contact with the external surface of a magnetic screw made of NdFeB or NdFeB compound;

FIG. 4B is a diagrammatic view that shows the magnetic field expressed in Gauss in contact with the external surface of an implant where the magnetic screw of FIG. 4A is inserted;

FIG. 4C is a diagrammatic view that shows the magnetic field expressed in Gauss at 1 millimeter (mm) distance from the surface of the implant of FIG. 4B.

Figure 5:
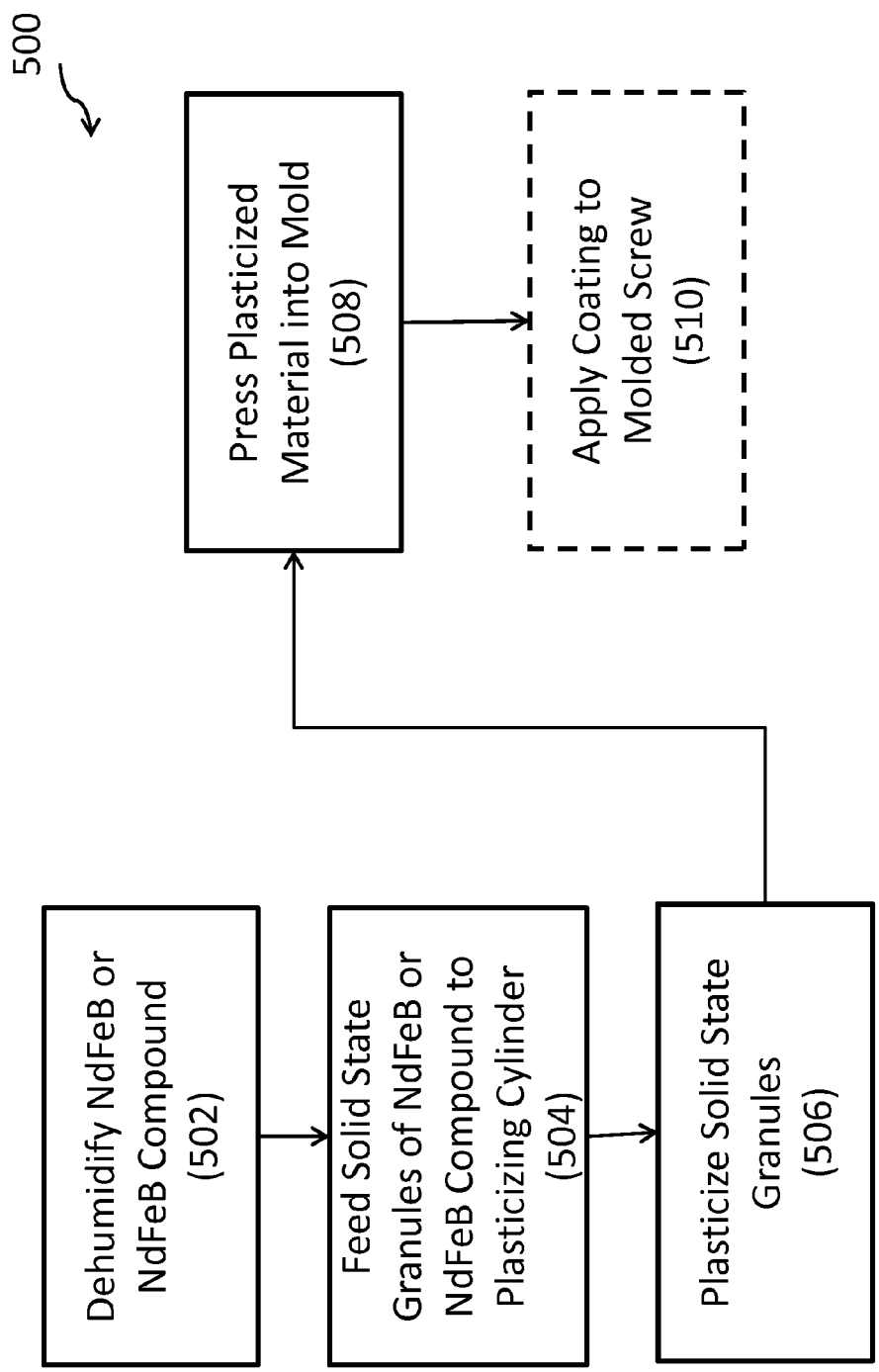
FIG. 5 is a flow chart of a method of making a screw of at least one embodiment of the invention.

Referring to FIGS. 1A and 1B, at least one embodiment of the invention is composed of a traditional implant (1) for dental prostheses. The installation (1) includes an empty metal cylindrical pin provided with wall with external thread (3) and axial cavity (1a) with internal thread accessible from above.

The second component of the apparatus consists in a corresponding metal covering screw (4), provided with threaded stem (4a) adapted to be engaged on the internal threaded walls (1a) of said implant (1).

In some embodiments, the covering screw (4) is made of NdFeB (Neodymium-Iron-Boron) permanent magnet.

In some embodiments, the covering screw (4) comprises an NdFeB compound comprising NdFeB, silicon and polyamide 12 (PA12) in addition to neodymium, iron and boron. PA 12 is a linear, semicrystalline-crystalline thermoplastic derivative of butadiene. PA12 exhibits electrical insulation properties and low-sensitivity to humidity. PA12 has high chemical stability. PA 12 has a lower concentration of amides compared to other available polyamide compositions. PA 12 also has a strong resistance to cracking under stress and higher dimension stability compared to other available polyamide compositions.

In some embodiments, an amount of neodymium in the NdFeB compound ranges from 29 weight % to 32 weight %. In some embodiments, an amount of iron in the NdFeB compound ranges from 59 weight % to 64 weight %. In some embodiments, an amount of boron in the NdFeB compound ranges from 4 weight % to 6 weight %. In some embodiments, an amount of silicon in the NdFeB compound ranges from 0.5 weight % to 1 weight %. In some embodiments, an amount of PA 12 ranges from 4.5 weight % to 5 weight %.

Because of magnetic properties of NdFeB or the NdFeB compound, a similar covering screw (4) can generate a magnetic field all around the implant (1) that favors a faster reconstitution of the surrounding bone tissue.

The covering screw (4) is provided with a thin head and is usually "coated" with the gingival mucosa (M) for the entire time that is necessary for consolidation of the implant (1) in the bone.

Now the screw (4) can be normally removed, after making an incision on the mucosa (M) to leave space to the threaded stem of a final stump.

FIGS. 2A and 2B show at least one embodiment of the invention that comprises, instead of said covering screw (4), a magnetic healing screw (14) provided with threaded stem (14a) adapted to be engaged on the internal threaded walls (1a) of the implant (1).

In particular, FIG. 2B shows that the head of said healing screw (14) is given high thickness in such a way that, once the healing screw is installed, the healing screw usually remains "outside" the gingival mucosa (M).

FIGS. 3A and 3B show at least one embodiment of the invention that comprises, instead of said covering screw (4) or said healing screw (14), a magnetic retention screw (24) adapted to be engaged on the internal threaded walls (1a) of the implant (1), after crossing an axial hole obtained on a corresponding stump (10).

In particular, FIG. 3A is an exploded view of said screw (24) before the screw is inserted in the corresponding stump (10), whereas FIG. 3B shows the same screw in operating condition, in which the screw fixes the stump (10) to the implant (1). Referring to FIG. 4A, the magnetic screw (4) is entirely made of NdFeB or NdFeB compound guarantees a maximum magnetic field of 1500 G, exactly in a lower end.

Referring to FIG. 4B, when the screw (4) is inserted in the implant (1), the minimum magnetic field on the external surface of the implant is at the lower end of the implant and is 80 G. In fact, a higher thickness of the implant (1) is in the lower part.

Referring to FIG. 4C, a magnetic field of 50 Gauss is obtained at 1 mm distance from the lower surface of the implant (1), which is sufficient to obtain the desired healing effects of the bone. Therefore, the present invention is efficacious for magnetic fields equal to or higher than 50 Gauss at a 1 mm distance from the external surface of the implant. Advantageously, in order to obtain such a result, a maximum thickness of the implant must be lower than 10 mm.

The magnetic inserts and keepers provide magnetic fields lower than 50 G at 1 mm distance from the implant.

FIG. 5 is a flow chart of a method 500 of making a screw of at least one embodiment of the invention. In some embodiments, the screw made by method 500 is a covering screw such as covering screw (4) (FIGS. 1A-1B). In some embodiments, the screw made by method 500 is a magnetic healing screw such as magnetic healing screw (14) (FIGS. 2A-2B). In some embodiments, the screw made by method 500 is a magnetic retention screw such as magnetic retention screw (24) (FIGS. 3A-3B).

In operation 502, the NdFeB or NdFeB compound material is dehumidified. In some embodiments, the dehumidifying comprises drying the NdFeB or NdFeB compound for a period of at least 2 hours at a temperature of at least 100° C. In some embodiments, the NdFeB or NdFeB compound is in the form of granules during the dehumidification process. In some embodiments, the NdFeB or NdFeB compound is granulated following the dehumidification process.

In operation 504, solid state granules of the NdFeB or NdFeB compound material are fed into a plasticizing cylinder. In some embodiments, the solid state granules are fed into the plasticizing cylinder using a hopper, a funnel or other suitable feeding mechanism. In some embodiments, the plasticizing cylinder includes an inner plasticizing screw configured to exert force on the granules to drive the granules from a receiving end to an exit end of the plasticizing cylinder. In some embodiments, the plasticizing cylinder further includes an outer wall containing electrical resistance elements. The electrical resistance elements are configured to generate heat in response to application of an electrical signal.

In operation 506, the solid state granules are plasticized in the plasticizing cylinder to form a plasticized material. In some embodiments, the NdFeB or NdFeB compound is heated to a temperature of about 250° C. In some embodiments, the NdFeB or NdFeB compound is heated to a temperature ranging from about 230° C. to about 260° C. If the NdFeB or NdFeB compound is not sufficiently heated, a density and viscosity of the plasticized material will be too great to completely fill a mold, in some instances. If the NdFeB or NdFeB compound is heated too much, the NdFeB or NdFeB compound will begin to separate or oxidize, in some instances.

In operation 508, the plasticized material is pressed into a mold. The mold is configured to define a shape of the screw. The mold includes an inner surface having a same substantially the same as the inner surface of the implant. In some embodiments, the shape the inner surface of the mold is adjusted from the shape of the inner surface of the implant to account for a coating to be formed on the screw.

In some embodiments, the plasticized material is pressed into the mold using an extruder. In some embodiments, the plasticized material is pressed into the mold using a pump or other suitable pressure exerting mechanism. In some embodiments, a pressure exerted on the plasticized material at the exit end of the plasticizing cylinder is about 1000 kg/cm2. In some embodiments, a pressure exerted on the plasticized material at an entrance to the mold is about 500 kg/cm2. If the insufficient pressure is exerted on the plasticized material, the plasticized material will not completely fill the mold due to the density and viscosity of the plasticized material, in some instances. If too great of pressure is exerted on the plasticized material, the mold will be damaged, in some instances. Completely filling the mold helps to ensure threads are accurately imparted to an outer surface of the screw during the molding process. As described above, the threads engage with the inner surface of the implant during insertion of the screw into the implant.

In optional operation 510, a coating is applied to the molded screw. The coating helps to prevent oxidation of the screw while the screw is in operating condition. In some embodiments, the coating is applied by physical vapor deposition. In some embodiments, the coating is applied by plating or other suitable coating processes. In some embodiments, the coating process is omitted.

One aspect of this description relates to a dental implant apparatus. The dental implant apparatus includes an implant having an external threaded wall adapted to be implanted in a patient's bone, said implant being provided with a cylindrical axial cavity having an internal thread accessible from a first end. The dental implant apparatus further includes a screw comprising a threaded stem adapted to be helicoidally coupled with the internal thread of said cavity of the implant, wherein said screw is a single piece made entirely of an NdFeB (Neodymium-Iron-Boron) compound comprising silicon.

Another aspect of this description relates to a method of making a screw for a dental implant. The method includes plasticizing an NdFeB compound comprising silicon, plasticizing the NdFeB compound comprises using a plasticizing cylinder. The method further includes molding the plasticized NdFeB compound using a mold to form the screw, the mold comprising a threaded inner surface.

Still another aspect of this description relates to a screw. The screw includes a threaded stem adapted to be helicoidally coupled with an internal thread of a cavity of an implant. The screw is a single piece made entirely of a NdFeB (Neodymium-Iron-Boron) compound including 29 weight % to 32 weight % neodymium; 59 weight % to 64 weight % iron; 4 weight % to 6 weight % boron; and 0.5 weight % to 1 weight % silicon.

It will be readily seen by one of ordinary skill in the art that the disclosed embodiments fulfill one or more of the advantages set forth above. After reading the foregoing specification, one of ordinary skill will be able to affect various changes, substitutions of equivalents and various other embodiments as broadly disclosed herein. It is therefore intended that the protection granted hereon be limited only by the definition contained in the appended claims and equivalents thereof.

What is claimed is:

1. A method of making a screw for a dental implant, the method comprising:
   plasticizing a NdFeB compound comprising silicon, plasticizing the NdFeB compound comprises using a plasticizing cylinder; and
   molding the plasticized NdFeB compound using a mold to form the screw, the mold comprising a threaded inner surface.

2. The method of claim 1, wherein plasticizing the NdFeB compound comprises heating the NdFeB compound to a temperature ranging from 230° C. to 260° C.

3. The method of claim 1, further comprising dehumidifying the NdFeB compound prior to plasticizing the NdFeB compound, wherein dehumidifying the NdFeB compound comprises heating the NdFeB compound at a temperature of at least 100° C. for at least 2 hours.

4. The method of claim 1, further comprising pressing the plasticized NdFeB compound into the mold, wherein pressing the plasticized NdFeB compound into the mold comprises exerting a pressure on the NdFeB compound at an exit end of the plasticizer cylinder of about 1000 kg/cm$^2$ and exerting a pressure on the NdFeB compound at an entrance of the mold of about 500 kg/cm$^2$.

5. The method of claim 1, further comprising coating the molded screw with a thin coating layer of a least one of nickel, copper, zinc, tin, silver, gold, titanium, or resins.

6. The method of claim 1, wherein plasticizing the NdFeB compound comprises plasticizing the NdFeB compound comprising:
   29 weight % to 32 weight % neodymium;
   59 weight % to 64 weight % iron;
   4 weight % to 6 weight % boron; and
   0.5 weight % to 1 weight % silicon.

7. The method of claim 1, wherein said screw is a covering screw having a thin head adapted to be coated by the patient's gingival mucosa.

8. The method of claim 1, wherein said screw is a healing screw having a head having sufficient height to remain outside the patient's gingival mucosa.

9. The method of claim 1, wherein said screw is a retention screw adapted to fix a stump to an implant.

* * * * *